US006955891B2

(12) United States Patent
Cunningham et al.

(10) Patent No.: US 6,955,891 B2
(45) Date of Patent: Oct. 18, 2005

(54) **REAGENTS FOR ASSAYING *BACILLUS ANTHRACIS* LETHAL FACTOR PROTEASE**

(75) Inventors: Barry R. Cunningham, Scotch Plains, NJ (US); Richard T. Cummings, Fanwood, NJ (US); Jeffrey D. Hermes, Warren, NJ (US); Scott Salowe, Dayton, NJ (US)

(73) Assignee: Merck & Co., Inc., Rahway, NJ (US)

( * ) Notice: Subject to any disclaimer, the term of this patent is extended or adjusted under 35 U.S.C. 154(b) by 10 days.

(21) Appl. No.: 10/424,954

(22) Filed: Apr. 28, 2003

(65) Prior Publication Data

US 2004/0019182 A1 Jan. 29, 2004

Related U.S. Application Data

(63) Continuation of application No. PCT/US03/05553, filed on Feb. 21, 2003.

(60) Provisional application No. 60/359,707, filed on Feb. 25, 2002.

(51) Int. Cl.$^7$ ............................ C12Q 1/04; C12Q 1/00; C07K 14/32; C07K 1/00; A61K 38/04

(52) U.S. Cl. ............................ 435/34; 435/4; 530/300; 530/324; 530/325; 530/326; 530/806

(58) Field of Search ....................... 435/4, 34; 530/300, 530/324, 325, 326, 806

(56) References Cited

U.S. PATENT DOCUMENTS

2002/0076741 A1 * 6/2002 Tencza ........................ 435/23

FOREIGN PATENT DOCUMENTS

WO WO 99/50439 10/1999
WO WO 01/59149 8/2001

OTHER PUBLICATIONS

Park, S. et al. "Optimized Production and Purification of *Bacillus anthracis* Lethal Factor", Protein Expression and Purification, 2000, vol. 18, pp. 293–302.

Clegg, R, "Fluorescence resonance energy transfer", Current Opinion in Biotechnology, 1995, vol. 6, pp. 103–110.

Cummings, R. et al. "A peptide–based fluorescence resonance energy transfer assay for *Bacillus anthracis* lethal factor protease", Proc. Natl. Acad. Sci. USA, 2002, vol. 99, pp. 6603–6606.

Dixon, T. et al. "Anthrax", New England Journal of Medicine, 1999, vol. 341, pp. 815–826.

Duesbery, N. et al. "Proteolytic Inactivation of MAP–Kinase–Kinase by Anthrax Lethal Factor", Science, 1998, vol. 280, pp. 734–737.

Hammond, S. et al. "Lethal Factor Active–Site Mutations Affect Catalytic Activity In Vitro", Infection and Immunity, 1998, vol. 66, pp. 2374–2378.

Mock, M. et al. "Anthrax", Annual Review of Microbiology, 2001, vol. 55, pp. 647–671.

Pannifer, A. et al. "Crystal structure of the anthrax lethal factor", Nature, 2001, vol. 414, pp. 229–233.

Selvin, P. "The renaissance of fluorescence resonance energy transfer", Nature Structural Biology, 2000, vol. 7, pp. 730–734.

Vitale, G. et al. "Anthrax Lethal Factor Cleaves the N–Terminus of MAPKKs and Induces Tyrosine/Threonine Phosphorylation of MAPKs in Cultured Macrophages", Biochemical and Biophysical Research Communications, 1998, vol. 248, pp. 706–711.

Vitale, G. et al. "Susceptibility of mitogen–activated protein kinase kinase family members to proteolysis by anthrax lethal factor", Biochem. J., 2000, vol. 352, pp. 739–745.

Wu, P. et al. "Resonance Energy Transfer: Methods and Applications", Analytical Biochemistry, 1994, vol. 218, pp. 1–13.

Zhang, J. et al. "A Simple Statistical Parameter for Use in Evaluation and Validation of High Throughput Screening Assays", Journal of Biomolecular Screening, 1999, vol. 4, pp. 67–73.

* cited by examiner

*Primary Examiner*—Ralph Gitomer
*Assistant Examiner*—Kailash C. Srivastava
(74) *Attorney, Agent, or Firm*—Sheldon O. Heber; Jack L. Tribble

(57) ABSTRACT

The present invention features a *Bacillus anthracis* lethal factor substrate. The substrate can be used for example to measure lethal factor activity. Preferred substrates contain one or mare detectable labels and have a sufficiently high turnover rate for applications in a high throughput screen.

10 Claims, 2 Drawing Sheets

REAGENTS FOR ASSAYING *BACILLUS ANTHRACIS* LETHAL FACTOR PROTEASE

CROSS-REFERENCE TO RELATED APPLICATIONS

The present application is a continuation application of PCT/US03/05553, filed Feb. 21, 2003, designating the U.S., which claims priority to provisional application U.S. Ser. No. 60/359,707, filed Feb. 25, 2002, hereby incorporated by reference herein.

BACKGROUND OF THE INVENTION

The references cited throughout the present application are not admitted to be prior art to the claimed invention.

Anthrax is a bacterial infection produced by *Bacillus anthracis*. *Bacillus anthracis* endospores can enter the body through skin abrasions, inhalation, or ingestion. *Bacillus anthracis* produces an anthrax toxin that is often lethal. (Dixon et al., (1999) *N. Engl. J. Med.* 341, 815–26.)

Anthrax toxin consists of three proteins, a receptor-binding component designated protective antigen, and two enzymatic components termed edema factor and lethal factor ("LF"). (Mock et al., (2001) *Annu. Rev. Microbiol.* 55, 647–71.) Lethal factor is a zinc-dependent metalloprotease that appears to exert toxic affects by cleaving mitogen-activated protein kinase kinases (MKKs). (Vitale et al., (1998) *Biochem. Biophys. Res. Commun.* 248, 706–11, Vitale et al., (2000) *Biochem. J.* 352 Pt 3, 739–45, Duesbery et al., (1998) *Science* 280, 734–7, Duesbery et al., International Publication No. WO 99/50439, International Publication Date Oct. 7, 1999.)

Vitale and co-workers have used microsequencing to identify the site in different MKKs that are cleaved by lethal factor. (See Table 1, Vitale et al., (2000) *Biochem. J.* 352 Pt 3, 739–45.) Lethal factor cleavage of different MKKs occurred within the N-terminal region preceding the kinase domain. Alignment of the sequences flanking the cleavage site revealed some consensus motifs: a hydrophobic residue in position P2 and P1', and at least one basic residue between P4 and P7. (Vitale et al., (2000) *Biochem. J.* 352 Pt 3, 739–45.)

Lethal factor has been indicated to cleave synthetic peptides in vitro. (Hammond et al., (1998) *Infect. Immun.* 66, 2374–8.) In vitro cleavage was inhibited by 1,10-phenanthroline or 10 mM EDTA, both of which chelate zinc.

SUMMARY OF THE INVENTION

The present invention features a *Bacillus anthracis* lethal factor substrate and assays employing the substrate to measure lethal factor activity and to screen for compounds affecting lethal factor activity. Preferred substrates contain one or more detectable labels and have a sufficiently high turnover rate to be suitable for use in a high throughput screen.

Thus, a first aspect of the present inventions features a peptide consisting essentially of:

$$X^1\text{-}X^2\text{-}X^3\text{-}X^4\text{-}X^5\text{-}X^6\text{-}X^7\text{-}X^8\text{-}X^9\text{-}X^{10}\text{-}X^{11}\text{-}X^{12}\text{-}X^{13}\text{-}X^{14}\text{-}X^{15}\text{-}X^{16}\text{-}X^{17}\text{-}X^{18}\text{-}X^{19}$$

wherein $X^1$ is either norleucine or a labeled derivative thereof;

$X^2$ is either proline, lysine, or a labeled derivative thereof;
$X^3$ is either lysine or a labeled derivative thereof;
$X^4$ is either lysine or a labeled derivative thereof;
$x^5$ is either lysine or a labeled derivative thereof;
$X^6$ is either proline, valine, or a labeled derivative thereof;
$X^7$ is either threonine, leucine, or a labeled derivative thereof;
$X^8$ is either proline or a labeled derivative thereof;
$X^9$ is either isoleucine or a labeled derivative thereof;
$X^{10}$ is either glutamine or a labeled derivative thereof;
$X^{11}$ is either leucine or a labeled derivative thereof;
$X^{12}$ is either asparagine or a labeled derivative thereof;
$X^{13}$ is either proline, alanine, or a labeled derivative thereof;
$X^{14}$ is either alanine or a labeled derivative thereof;
$X^{15}$ is either proline, threonine, or a labeled derivative thereof;
$X^{16}$ is either aspartic acid or a labeled derivative thereof;
$X^{17}$ is either lysine, cysteine, or a labeled derivative thereof;
$X^{18}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a labeled derivative thereof;
$X^{19}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a labeled derivative thereof; and
"z" is either an amide linkage or an ester linkage.

Reference to "consisting essentially" or "consist essentially" with respect to a peptide indicate that additional groups may be present that do not significantly prevent the peptide from acting as a lethal factor substrate. Examples of additional groups include one more of the following: salts, additional amino acid(s) at the N-terminus, additional amino acid(s) at the C-terminus, and protecting group(s).

Unless otherwise indicated, reference to an amino acid having a chiral center refers to the L-enantiomer; and amino acids are joined by peptide (amide) linkages.

Reference to a "labeled derivative" of an amino acid indicates that the amino acid is modified with a chemical moiety (also referred herein as a label) that can be detected or specifically bound by another molecule and which does not significantly prevent the peptide from acting as a lethal factor substrate. Detection can be by direct means, such as the moiety producing a detectable signal; or by indirect means such as by the moiety serving as binding site for another moiety that emits a signal.

Another aspect of the present invention features a method of measuring *Bacillus anthracis* lethal factor activity. The method comprises the steps of: (a) incubating lethal factor and a lethal factor substrate using an incubation medium wherein the lethal factor is active; and (b) measuring cleavage of the peptide.

Another aspect of the present invention features a method of measuring the ability of a compound to affect *Bacillus anthracis* lethal factor activity. The method comprises the steps of: (a) incubating the compound, lethal factor, and a lethal factor substrate using an incubation medium wherein the lethal factor is active; and (b) measuring cleavage of the peptide.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

Figure 1:
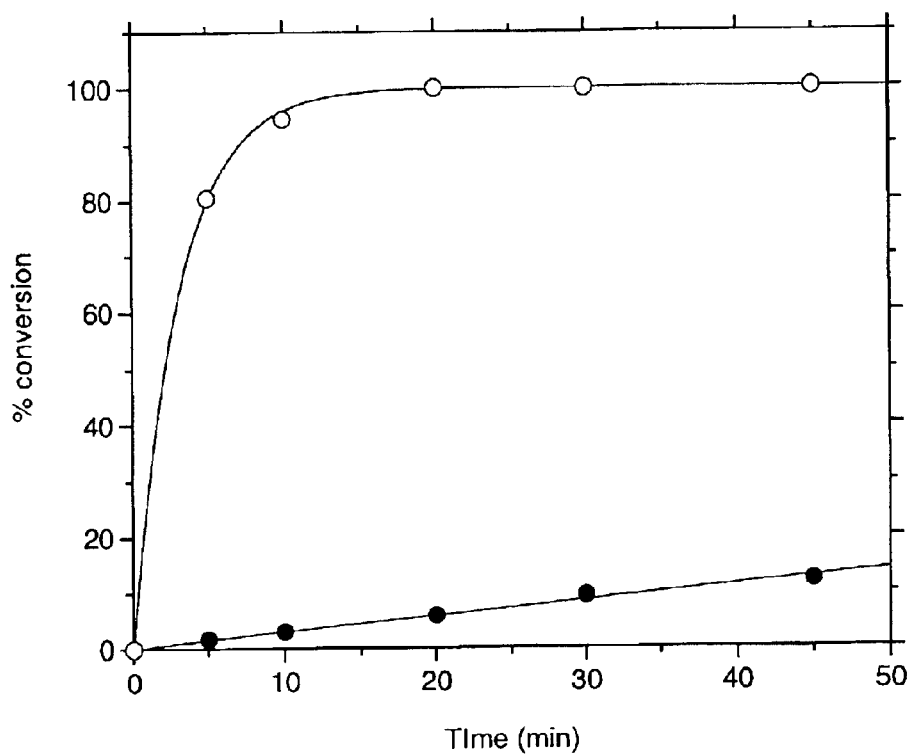
FIG. 1 illustrates the results of enzymatic cleavage experiments using fluoresceinated substrates [Nle$^1$]Mek $1_{1-16}$(KGG)-NH$_2$ (SEQ ID NO: 1) and the MKK consensus sequence analog (Flu)NleKKKKVLPIQLNAATDKGG-NH$_2$ (SEQ ID NO: 2) as assessed by the HPLC cleavage assay. [Substrate]=100 $\mu$M, [LF]=1 $\mu$M, T=37° C. with time points as indicated. [Nle$^1$]Mek$1_{1-16}$(KGG)-NH$_2$ (SEQ ID NO: 1) substrate consumption is illustrated by closed circles. MKK consensus sequence analog substrate consumption is illustrated by open circles. First-order rate constants were derived from curve fitting each set of data; comparison of these rate constants indicated that the turnover of the consensus sequence was ~100-fold faster than the MEK1 sequence.

The present invention features a *Bacillus anthracis* lethal factor substrate and assays employing the substrate to measure lethal factor activity and to screen for compounds affecting such activity. Assaying lethal factor activity can be used to better characterize and study such activity and to obtain lethal factor inhibitory compounds.

Lethal factor inhibitor compounds can be used to further study lethal factor activity, and those inhibitory compounds having appropriate pharmacological properties can be used to help treat or prevent Anthrax. Appropriate pharmacological properties include efficacy, metabolism and absence of unacceptable side effects.

High throughput screening for lethal factor inhibitors can be used to screen large number of compounds to identify those affecting lethal factor activity. High throughput screening is facilitated by an assay that is readily automated and utilizes low levels of purified enzyme.

Preferred substrates contain one or more detectable labels and have a sufficiently high turnover rate and low background rate to be suitable for use in a high throughput screen. Preferred substrates can be used with low nanomolar amounts (in the range of 1–10 nM) of enzyme with short incubation times (5–60 minutes), using a multi-well plate-based format.

Lethal Factor Substrate

Lethal factor substrates described herein consist essentially of:

$X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$ wherein $X^1$ is either norleucine or a labeled derivative thereof;

$X^2$ is either proline, lysine, or a labeled derivative thereof; preferably, $X^2$ is either lysine or a labeled derivative thereof;

$X^3$ is either lysine or a labeled derivative thereof;

$X^4$ is either lysine or a labeled derivative thereof;

$X^5$ is either lysine or a labeled derivative thereof;

$X^6$ is either proline, valine, or a labeled derivative thereof; preferably $X^6$ is either valine or a labeled derivative thereof;

$X^7$ is either threonine, leucine, or a labeled derivative thereof; preferably, $X^7$ is either leucine or a labeled derivative thereof;

$X^8$ is either proline or a labeled derivative thereof;

$X^9$ is either isoleucine or a labeled derivative thereof;

$X^{10}$ is either glutamine or a labeled derivative thereof;

$X^{11}$ is either leucine or a labeled derivative thereof;

$X^{12}$ is either asparagine or a labeled derivative thereof;

$X^{13}$ is either proline, alanine, or a labeled derivative thereof; preferably, $X^{13}$ is either alanine or a labeled derivative thereof;

$X^{14}$ is either alanine or a labeled derivative thereof;

$X^{15}$ is either proline, threonine, or a labeled derivative thereof; preferably, $X^{15}$ is either threonine or a labeled derivative thereof;

$X^{16}$ is either aspartic acid or a labeled derivative thereof;

$X^{17}$ is either lysine, cysteine, or a labeled derivative thereof; preferably, $X^{17}$ is either lysine or a labeled derivative thereof;

$X^{18}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a labeled derivative thereof; preferably, $X^{18}$, is glycine or a labeled derivative thereof;

$X^{19}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a labeled derivative thereof; preferably, $X^{19}$, is glycine or a labeled derivative thereof; and "z" is either an amide linkage or an ester linkage.

Techniques for chemical synthesis of peptides are well known in the art. (See e.g., Vincent, in *Peptide and Protein Drug Delivery*, New York, N.Y., Dekker, 1990, and the Example 1, infra.)

Preferred positions for labeled derivatives depend upon the label. Labels should be chosen so as not to significantly affect the ability of the substrate to be cleaved by lethal factor. Small labels such as radioactive labels are not expected to affect cleavage. Bulky labels at or near the cleavage site may affect cleavage. The effect of a particular label on cleavage can readily be evaluated by assaying for cleavage.

The cleavage site for the lethal factor substrates described herein is between $X^8$ proline and $X^9$ isoleucine. In different embodiments there is no label at a cleavage site amino acid, there is no label within one amino acid from the cleavage site (i.e., no label at a cleavage site amino acid or at a neighboring amino acid), there is no label within two, three, four, five, six, or seven amino acids from the cleavage site; only $X^1$ and/or $X^{17}$ contain a label; and there is no label. In a separate embodiment z is an amide linkage.

Table I provides examples of different lethal factor substrates.

TABLE I

| Seq ID No | Designation | Peptide |
|---|---|---|
| 7 | (Flu)MEK1$_{1-16}$-NH$_2$ | (Flu)MPKKKPTP IQLNPAPD-NH$_2$ |
| 1 | (Flu) [Nle$^1$]MEK1$_{1-16}$(KGG)-NH$_2$ | (Flu)NlePKKKPTP IQLNPAPDKGG-NH$_2$ |
| 2 | (Flu)Consensus (KGG)-NH$_2$ | (Flu)NleKKKKVLP IQLNAATDKGG-NH$_2$ |
| 3 | (Cou)Consensus (K(Q-35)GG)-NH$_2$ | (Cou)NleKKKKVLP IQLNAATDK(Q-35)GG-NH$_2$ |
| 5 | (Cou)Consensus (K(DAB)GG)-NH$_2$ | (Cou)NleKKKKVLP IQLNAATDK(DAB)GG-NH$_2$ |
| 4 | (Q-35)Consensus (K(Cou)GG)-NH$_2$ | (Q-35)NleKKKKVLP IQLNAATDK(Cou)GG-NH$_2$ |
| 6 | (DAB)Consensus (K(Cou)GG)-NH$_2$ | (DAB)NleKKKKVLP IQLNAATDK(Cou)GG-NH$_2$ |

Flu = 5,6-carboxyfluoresceinyl
Cou = 7-hydroxy-4-methyl-3-acetylcoumarinyl
DAB = 4-dimethylaminoazobenzene-4'-carboxyl
Q-35 = N-({4-[(7-nitro-2,1,3-benzoxadiazol-4-yl)amino]phenyl}acetyl Standard one and three letter codes for amino acids are as follows: Nle=norleucine; A=Ala=Alanine: C=Cys=Cysteine: D=Asp=Aspartic acid: E=Glu=Glutamic acid: F=Phe=Phenylalanine: G=Gly=Glycine: H=His=Histidine: I=Ile=Isoleucine: K=Lys=Lysine: L=Leu=Leucine: M=Met=Methionine: N=Asn=Asparagine: P=Pro=Proline: Q=Gln=Glutamine: R=Arg=Arginine: S=Ser=Serine: T=Thr=Threonine: V=Val=Valine: W=Trp=Tryptophan: and Y=Tyr=Tyrosine.

Assay Formats

A variety of different assay formats can be employed to detect peptide cleavage. Homogeneous assays detect the cleavage product without separation of the materials through a direct readout such as FRET or by an alternate detection such as an antibody raised to a cleavage fragment. Heterogenous assays detect the cleavage product after separating the cleaved peptide fragments from one another through some mechanism such as avidin capture of a biotin labeled material or separation by physical properties such as occurs on an HPLC column.

Assays can be performed employing a variety of different labels such as a fluorescent moiety, a quencher moiety, a chemiluminescent moiety, a radioisotope, biotin, biotin derivatives, lanthanides, and antibody specific tags such as anti-phosphotyrosine, anti-phosphoserine, anti-dinitrophenyl, anti-FLAG, anti-fluorescein, anti-rhodamine, and anti-digoxigenin.

One or more labels, which may be the same or different, can be present on one or both sides of the cleavage site. Single side label(s) can be used in instances where substrates and products separate based on physical properties (such as in HPLC) or when substrate cleavage generates a site for specific recognition of a product, for example by an antibody.

Labels on opposite sides of the cleavage site can be used in multiple ways. In homogenous formats these labels can interact such that signal will increase or decrease upon substrate cleavage. An example of a homogeneous signal increase format is an assay employing an internally quenched FRET pair. In heterogeneous formats the separation of a product from substrate by one label allows specific detection of a cleavage product by the other label.

An acceptor and donor FRET pair present on opposite sides of a cleavage site produce a different signal depending upon whether cleavage has taken place. In the absence of cleavage, a donor excited by a suitable light source emits energy having the proper wavelength to absorbed by the acceptor. The acceptor quenches signal production from the donor by either emitting light at a different wavelength (if the acceptor is another fluorophore) or by dissipating the energy to the environment (if the acceptor is a quencher).

FRET assays can be run assaying for the appearance of donor fluorescence if the acceptor is a quencher since upon cleavage donor and quencher are separated. Alternatively, if both donor and acceptor are fluorophores and the donor is being excited, FRET assays can be run assaying for the appearance of donor fluorescence or the disappearance of acceptor fluorescence.

A variety of different fluorophores and quenchers are well known in the art. Examples of fluorophores include dansyl and its derivatives, fluorescein and its derivatives, rhodamine and its derivatives, Texas Red, coumarin derivatives, Cy dyes, AlexaFluor dyes (Molecular Probes), and BODIPY dyes (Molecular Probes). Examples of quencher includes the QSY series (Molecular Probes), Dabcyl, p-nitrophenyl derivatives, dinitrophenyl derivatives, and the Cy quencher dyes (Amersham-Pharmacia). Techniques and reagents for performing FRET are well known in the art. (For example, see, Selvin, (2000) *Nat. Struct. Biol.*, 7(9), 730–4, Clegg, (1995) *Curr. Opin. Biotechnol.*, 6(1), 103–10, 1995, and Wu et al., *Anal. Biochem.*, 218(1), 1–13, 1994.)

With appropriately labeled substrates alternate technologies can be used to measure substrate cleavage. Examples of homogeneous formats would include fluorescence polarization, time resolved FRET, SPA™, FlashPlate™, and AlphaScreen™. Examples of heterogenous formats would include DELFIA™, chemiluminescence plate based assays, HPLC, radioactive filter binding assays, absorbance assays, and fluorescence assays.

Measuring Activity

Lethal factor substrates can be used in methods measuring *Bacillus anthracis* lethal factor activity and the effect of a compound on such activity. Such methods involve incubating a lethal factor substrate described herein with *Bacillus anthracis* lethal factor using an incubation medium where the *Bacillus anthracis* lethal factor is active, and can include the presence of a compound being tested. Cleavage of the substrate can be detected as a measure of *Bacillus anthracis* lethal factor activity or the effect of a compound on lethal factor activity. Measuring can be qualitative or quantitative.

EXAMPLES

Examples are provided below to further illustrate different features of the present invention. The examples also illustrate useful methodology for practicing the invention. These examples do not limit the claimed invention.

Example 1

Materials and Methods

This example describes different materials and methods that were employed to produce and study lethal factor substrates.

Substrate Synthesis Peptide synthesis was carried out on an ABI Model 433A Peptide Synthesizer employing FastMoc™ chemistry with increased acylation times on a 250 μmol scale. All reagents, including amino acids, were from PE Applied Biosystems except for (Fmoc)-L-Nle (Bachem), (Fmoc)-L-Lys(Mtt) (Novabiochem) and PL-Rink Resin (Polymer Laboratories). All fluorophores and quenchers were from Molecular Probes, Inc. (Eugene, Oreg.).

Peptide labeling with reporters was carried out on resin subsequent to peptide synthesis. Incorporation of materials at the N-terminus was accomplished by labeling with commercially available N-hydroxysuccinimidyl esters. Typical reactions were carried out on a 20–100 μmol resin scale using a 1–10 fold excess of the label in a minimal volume (1–3 mL) of N-methylpyrrolidinone overnight.

Incorporation of the two reporters for the FRET substrates was accomplished by first labeling the N-terminus. The second reporter was then introduced by selectively removing the Lys(Mtt) protecting group ($CH_2Cl_2$ with 2% TFA and 3% Triisopropylsilane, room temperature, 45 minutes), resin washing, and reaction with the label as described above.

After incorporation of appropriate reporters, the resin was washed with NMP, acetic acid, $CH_2Cl_2$, and methanol (3× each), dried briefly in vacuo and the peptides cleaved using 95% TFA/2.5% $H_2O$/2.5% Triisopropylsilane for 90 minutes. After precipitation from cold diethyl ether, the crude peptides were purified on a Waters PrepLC 4000 system using a 25×400 mm 300 Å DeltaPak $C_{18}$ column and a $CH_3CN/H_2O$ (both with 0.1% TFA) gradient. Purified peptides were lyophilized and their molecular weight confirmed by mass spectral analysis. All peptides were >95% pure by reversed-phase HPLC ($A_{214}$).

Lethal Factor HPLC-Based Assay

Peptides were prepared as 1 mM stock solutions in doubly distilled water. As long term solution stability has not been evaluated these materials were protected from incident light and used within a week of preparation. Test peptides were incubated at 100 μM with varying levels of lethal factor in 50 mM HEPES (pH 7.0)/20 mM NaCl/10 mM $MgCl_2$/100 μM $CaCl_2$/100 μM $ZnCl_2$/1 mg/ml BSA/1 mM DTT) for various times.

Prior to HPLC injection, samples were treated by precipitation of the protein materials by addition of a 10-fold excess volume of 60% $CH_3CN$ in $H_2O$. The samples were then vortexed, allowed to sit on ice for at least 15 minutes, centrifuged (2000 g×60 seconds), and the supernatant removed from the protein pellet. HPLC samples typically contained 150–300 ng (75–150 pmol) of labeled peptide. Peptide substrates and products were separated on a $C_{18}$ column (HAIPEEK Targa $C_{18}$ 5 μm, 20×2.1 mm, Higgins Analytical) using a $CH_3CN/H_2O$ (both with 0.1% TFA) gradient on a Waters 625 LC system with in-line UV-Vis (Waters 996) and fluorescence (Hitachi F-1050) detection. Fluorescence signals (excitation 445 nm/emission 520 nm) were integrated using Water's Millennium software.

Lethal Factor Plate-Based Assay

To each well of a 96-well black flat-bottomed plate (Packard) was added 25 μl of a 6 μM solution of the peptide substrate (Cou)Consensus(K(QSY-35)GG)-$NH_2$ (SEQ ID NO: 3) in assay buffer (20 mM HEPES (pH 7.0)/1 mM $CaCl_2$/0.1 mg/ml BSA/0.01% Tween-20). Test compounds in DMSO (1.5 μl) were added with additional assay buffer (18.5 μl) to the plate with a CyBi well dispenser. The enzymatic reaction was initiated with 30 μl of 10 nM lethal factor in assay buffer and terminated after 15 minutes at room temperature by the addition of 25 μl of 4 mM ortho-phenanthroline/40 mM EDTA, both steps being executed on a Tecan Genesis workstation. The fluorescence was read on a $Victor^2$ V plate reader using the umbelliferone protocol (excitation 355 nm/emission 460 nm).

Example 2

Labeled Peptide MEK1-Peptide Substrate

The fluoresceinated amide analog (Flu) MPKKKPTPIQLNPAPD-$NH_2$ (SEQ ID NO: 7) was employed to evaluate the ability of labeled lethal factor peptide to be cleaved by lethal factor. The N-terminal fluoresceinyl group provides a sensitive spectroscopic handle for HPLC analysis of the anticipated cleavage reaction. The presence of the N-terminal fluoresceinyl group also provides a large chromophore on the peptide's N-terminus allowing a determination as to whether large detectable labels are tolerated by lethal factor.

Experiments were preformed using (Flu) MPKKKPTPIQLNPAPD-$NH_2$ (SEQ ID NO: 7) incubated at 100 μM with various amounts of lethal factor in a metal ion supplemented buffer (see Example 1) similar to that found in Hammond et al., (1998) *Infect Immun* 66, 2374–8. Good levels of turnover (15–30%) were observed employing high levels of enzyme (~1μM) for extended periods (2–4 hours at 30° C.).

The anticipated products, those resulting from cleavage of the $Pro_8-Ile_9$ peptide bond, were detected by mass spectral analyses (data not shown). HPLC analysis was complicated by an unanticipated side reaction: a fluorescein-mediated oxidation of the methionine residue's sidechain to the corresponding sulfoxide. The product of this reaction (the Met(O) substrate) nearly co-eluted with the cleavage product, (Flu)MPKKKPTP(OH) (SEQ ID NO: 8), making analysis difficult. This oxidation occurred with peptide both as a solid and in solution, and was particularly rapid in solution in the presence of light with up to 50% conversion within one hour (data not shown).

Example 3

Enhanced MEK1-Peptide Substrate The peptide (Flu) NlePKKKPTPIQLNPAPDKGG-$NH_2$ ("[$Nle^1$]Mek1$_{1-16}$(KGG)-$NH_2$") (SEQ ID NO: 1) was produced to eliminate the oxidation side reaction and to facilitate peptide labeling at the C-terminus. [$Nle^1$]Mek1$_{1-16}$(KGG)-$NH_2$ (SEQ ID NO: 1) contains an N-terminus isostere norleucine rather than methionine; and incorporates -KGG- at its C-terminus with the lysyl residue being added as an Mtt protected amino acid. The differentially protected lysine provides a site for introduction of specific reporters via its selective deprotection while still on the resin. The glycyl residues were added in order to facilitate labeling by providing a spacer between the lysyl sidechain and the resin.

[$Nle^1$]Mek1$_{1-16}$(KGG)-$NH_2$ (SEQ ID NO: 1) was stable and showed no propensity towards oxidation. The peptide was cleaved by lethal factor between the $Pro_8-Ile_9$ bond (identified by mass spectral analysis) at a rate similar to the original peptide, indicating that the substitution of norleucine for methionine and the addition of three amino acids had no adverse effect on cleavage.

Example 4

Lethal Factor Substrate

This example describes the production of a "consensus" lethal factor substrate containing shared elements between the reported natural substrates. The consensus peptide had a significantly higher turnover rate than the MEK1-derived peptides described in Examples 2 and 3, facilitating its use in high throughput screening. The MEK1-derived peptide as a substrate in an assay of lethal factor proteolytic activity required a high concentration of enzyme required, even with long reactions times.

The peptide (Flu)NleKKKKVLPIQLNAATDKGG-NH$_2$ (SEQ ID NO: 2) was designed to reflect the common elements present in lethal factor substrates and to allow incorporation of reporters in an orthogonal manner. (Flu)NleKKKKVLPIQLNAATDKGG-NH$_2$ (SEQ ID NO: 2) differs from the [Nle$^1$]Mek1$_{1-16}$(KGG)-NH$_2$ (SEQ ID NO: 1)substrate at five positions. The three proline residues at positions 6, 13, and 15 were converted to residues found in the other MKK substrates in order to reduce the possibility of alternate cleavages adjacent to prolyl residues and to minimize potential secondary structure. The proline at the second position was converted to lysine for these reasons and to reflect the tetrabasic component of the consensus sequence. The threonine at position seven was converted to leucine, a residue found in five out of the eight known sequences. The -KGG- functionality was retained at the C-terminus.

Using the HPLC assay (Flu)NleKKKKVLPIQLNAATDKGG-NH$_2$ (SEQ ID NO: 2) was compared head-to-head with the [Nle$^1$]Mek1$_{1-16}$(KGG)-NH$_2$ (SEQ ID NO: 1) peptide. As shown in FIG. 1, (Flu)NleKKKKVLPIQLNAATDKGG-NH$_2$ (SEQ ID NO: 2) was a much better substrate, with an improvement in turnover number of approximately 100-fold. Mass spectral analysis confirmed that the appropriate cleavage was taking place.

Example 5
FRET Peptide Labels

Different fluorophores and quenchers were chosen and examined for their ease of synthesis, degree of quenching, and substrate suitability. Preferred pairs were a coumarin fluorophore (7-hydroxy-4-methyl-3-acetylcoumarinyl; $\lambda_{ex}$386 nm, $\lambda_{em}$448 nm) paired with either DABCYL (4-dimethylaminoazobenzene-4'-carboxyl; $\lambda_{max}$454 nm) or QSY-35®(N-({4-[(7-nitro-2,1,3-benzoxadiazol-4-yl)amino]phenyl}acetyl), $\lambda_{max}$475 nm) as the quencher.

Figure 2:
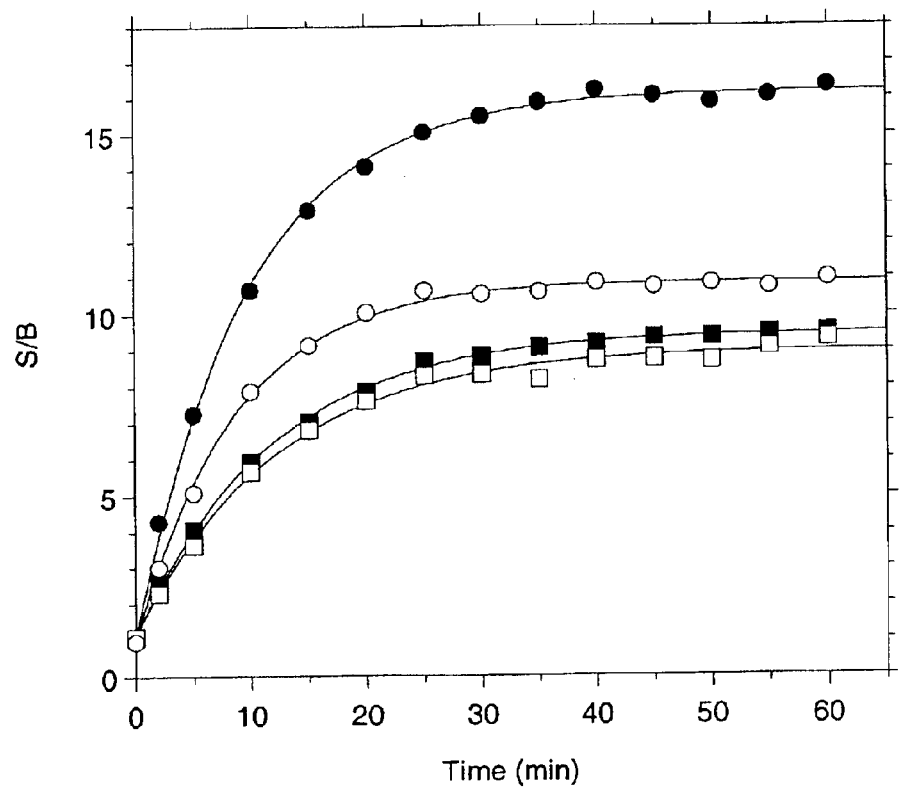
FIG. 2 illustrates results from enzymatic cleavage experiments of four FRET analogs of the MKK consensus sequence. Peptides at 10 $\mu$M in 50 mM HEPES (pH 7.0)/20 mM NaCl/10 mM MgCl$_2$/100 $\mu$M CaCl$_2$/100 $\mu$M ZnCl$_2$/1 mg/ml BSA/1 mM DTT were incubated with 100 nM lethal factor in a volume of 75 $\mu$l in a black 96-well plate. The increase in fluorescence (excitation 355 nm/emission 460 nm) was read on a Victor$^2$ V plate reader. (Cou)Consensus (K(QSY-35)GG)-NH$_2$ (SEQ ID NO: 3) (closed circles); (QSY-35)Consensus(K(Cou)GG)-NH$_2$ (SEQ ID NO: 4) (open circles); (Cou)Consensus(K(DAB)GG)-NH$_2$ (SEQ ID NO: 5) (closed squares); (DAB)Consensus(K(Cou)GG)-NH$_2$ (SEQ ID NO: 6) (open squares).

Analogs of the (Flu)NleKKKKVLPIQLNAATDKGG-NH$_2$ (SEQ ID NO: 2) were produced with the coumarin fluorophore at either the C- or N- terminus and one of the two quenchers at the distal end of the peptide. The analog reactivity with lethal factor was analyzed via the increase in fluorescence upon separation of fluorophore and quencher. As shown in FIG. 2, all four peptides cleaved at approximately the same rate with similar signal/background (S/B) varying between 9 and 16 at 100% cleavage. The progress curves were first order, indicating that the K$_m$s of the four substrates are >>10 $\mu$M. The peptide with the largest S/B, denoted (Cou)Consensus(K(QSY-35)GG)-NH$_2$, (SEQ ID NO: 3) was chosen for further studies.

The tested peptides included (Flu)NleKKKKVLPIQLNAATDK(QSY-9)GG-NH$_2$ (SEQ ID NO: 9) and (QSY-9)NleKKKKVLPIQLNAATDK(Flu)GG-NH$_2$ (SEQ ID NO: 10) where Flu=fluorescein and QSY-9 is a quencher from Molecular Probes, Inc. These peptides did not produce a good signal.

Example 6
Assay Optimization

A series of optimization experiments indicated that a simplified buffer consisting of only 20 mM HEPES (pH 7.0) and 1 mM CaCl$_2$ improved the enzyme activity more than ten-fold relative to the more complex buffer used earlier (Example 2). BSA and Tween-20 were added at low levels (0.1 mg/ml and 0.01%, respectively) to prevent adsorptive losses of enzyme and facilitate automated liquid handling.

Conversion of the continuous assay into a fixed time assay for plate based screening was achieved by terminating the reaction with 1 mM ortho-phenanthroline/10 mM EDTA. As described in Example 1, the assay is configured to run in 96-well plates with a 75 $\mu$l reaction volume followed by a 25 $\mu$l quench. While these volumes are convenient for both manual and automated liquid handling, there is room for miniaturization to higher density formats if desired.

An optimized protocol is described in Example 1, Lethal Factor Plate-Based Assay. Using the optimized protocol, the S/B was approximately 9 at 100% cleavage of 2 $\mu$M substrate; and 4 nM lethal factor leads to 40–50% cleavage in 15 minutes at room temperature for a typical assay S/B of ~4.

Since the reaction is first-order, the degree of inhibition by a test compound is a linear function of the reduction in the rate constant, not the reduction in the amount of product formed; however, for turnover <50% the correction is small and the percent inhibition is well approximated by the percent decrease in the net fluorescent signal.

As with other assays using a fluorophore at this wavelength, artifactual low signal (due to compound absorption) or high signal (due to compound fluorescence) can be encountered during screening. The use of longer wavelength fluorophore/quencher pairs should reduce such artifacts.

Other embodiments are within the following claims. While several embodiments have been shown and described, various modifications may be made without departing from the spirit and scope of the present invention.

What is claimed is:

1. A peptide consisting essentially of:

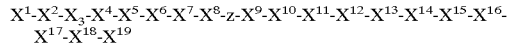

wherein $X^1$ is either norleucine or a $X^1$ labeled derivative thereof, provided that said $X^1$ labeled derivative is norleucine modified with a chemical moiety that can be detected or specifically bound by another molecule and which does not significantly prevent the peptide from acting as a lethal factor substrate;

$X^2$ is either proline, lysine, or a $X^2$ labeled derivative thereof, provided that said $X^2$ labeled derivative is proline or lysine modified with a chemical moiety that can be detected or specifically bound by another molecule and which does not significantly prevent the peptide from acting as a lethal factor substrate;

$X said $X^{18}$ labeled derivative is alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid modified with a chemical moiety that can be detected or specifically bound by another molecule and which does not significantly prevent the peptide from acting as a lethal factor substrate;

$X^{19}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a $X^{19}$ labeled derivative thereof, provided that said $X^{19}$ labeled derivative is alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid modified with a chemical moiety that can be detected or specifically bound by another molecule and which does not significantly prevent the peptide from acting as a lethal factor substrate; and z is either an amide linkage or an ester linkage.

2. The peptide of claim 1, wherein $X^1$ is either norleucine or said $X^1$ labeled derivative thereof;

$X^2$ is either lysine or said $X^2$ labeled derivative thereof;

$X^3$ is either lysine or said $X^3$ labeled derivative thereof;

$X^4$ is either lysine or said $X^4$ labeled derivative thereof;

$X^5$ is either lysine or said $X^5$ labeled derivative thereof;

$X^6$ is either valine or said $X^6$ labeled derivative thereof;

$X^7$ is either leucine or said $X^7$ labeled derivative thereof;

$X^8$ is either proline or said $X^8$ labeled derivative thereof;

$X^9$ is either isoleucine or said $X^9$ labeled derivative thereof;

$X^{10}$ is either glutamine or said $X^{10}$ labeled derivative thereof;

$X^{11}$ is either leucine or said $X^{11}$ labeled derivative thereof;

$X^{12}$ is either asparagine or said $X^{12}$ labeled derivative thereof;

$X^{13}$ is either alanine or said $X^{13}$ labeled derivative thereof;

X 14 is either alanine or said X 14 labeled derivative thereof;

$X^{15}$ is either threonine or said $X^{15}$ labeled derivative thereof;

$X^{16}$ is either aspartic acid or said $X^{16}$ labeled derivative thereof;

$X^{17}$ is either lysine, cysteine or said $X^{17}$ labeled derivative thereof;

$X^{18}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or said $X^{18}$ labeled derivative thereof;

$X^{19}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or said $X^{19}$ labeled derivative thereof; and "z" is either an amide linkage or an ester linkage.

3. The peptide of claim 1, wherein said peptide consists of:

$$X^1\text{-}X^2\text{-}X_3\text{-}X^4\text{-}X^5\text{-}X^6\text{-}X^7\text{-}X^8\text{-}z\text{-}X^9\text{-}X^{10}\text{-}X^{11}\text{-}X^{12}\text{-}X^{13}\text{-}X^{14}\text{-}X^{15}\text{-}X^{16}\text{-}X^{17}\text{-}X^{18}\text{-}X^{19}$$

wherein $X^1$ is labeled derivative of norleucine;

$X^2$ is lysine;

$X^3$ is lysine;

$X^4$ is lysine;

$X^5$ is lysine;

$X^6$ is valine;

$X^7$ is leucine;

$X^8$ is proline;

$X^9$ is isoleucine;

$X^{10}$ is glutamine;

$X^{11}$ is leucine;

$X^{12}$ is asparagine;

$X^{13}$ is alanine;

$X^{14}$ is alanine;

$X^{15}$ is threonine;

$X^{16}$ is aspartic acid;

$X^{17}$ is lysine or said $X^{17}$ labeled thereof;

$X^{18}$ is glycine; and $X^{19}$ is glycine-$NH^2$.

4. The peptide of claim 3, wherein said $X^1$ is norleucine labeled with 5, 6- carboxyfluoresceinyl and said $X^{17}$ is lysine.

5. The peptide of claim 3, wherein either:

a) said $X^1$ is norleucine labeled with 7-hydroxy-4-methyl-3-acetylcoumarinyl; and said $X^{17}$ is lysine labeled with either 4-dimethylaminoazobenzene-4'-carboxyl or N-({4-[(7-nitro-2,1,3-benzoxadiazol-4-yl)amino]phenyl}acetyl; or b) said $X^1$ is norleucine labeled with either 4-dimethylaminoazobenzene-4'-carboxyl or N-({4-[(7-nitro-2,1,3-benzoxadiazol-4-yl)amino]phenyl}acetyl; and said $X^{17}$ is lysine labeled with 7-hydroxy-4-methyl-3-acetylcoumarinyl.

6. The peptide of claim 5, wherein said $X^1$ is norleucine labeled with 7-hydroxy-4-methyl-3-acetylcoumarinyl and $X^{17}$ is lysine labeled with N-({4-[(7-nitro-2,1,3-benzoxadiazol-4-yl)amino]phenyl}acetyl.

7. The peptide of claim 1, wherein said peptide contains an acceptor and a donor fluorescence resonance energy transfer (FRET) pair on opposite sides of z, wherein either:

a) only one of said $X^1$ labeled derivative, said $X^2$ labeled derivative, said $X^3$ labeled derivative, said $X^4$ labeled derivative, said $X^5$ labeled derivative, said $X^6$ labeled derivative, said $X^7$ labeled derivative, and said $X^8$ labeled derivative is present and is said donor; and only one of said $X^9$ labeled derivative, said $X^{10}$ labeled derivative, said $X^{11}$ labeled derivative, said $X^{12}$ labeled derivative, said $X^{13}$ labeled derivative, said $X^{14}$ labeled derivative, said $X^{15}$ labeled derivative, said $X^{16}$ labeled derivative, said $X^{17}$ labeled derivative, said $X^{18}$ labeled derivative, and said $X^{19}$ labeled derivative is present and is said acceptor; or b) only one of said $X^1$ labeled derivative, said $X^2$ labeled derivative, said $X^3$ labeled derivative, said $X^4$ labeled derivative, said $X^5$ labeled derivative, said $X^6$ labeled derivative, said $X^7$ labeled derivative, and said $X^8$ labeled derivative is present and is said acceptor; and only one of said $X^9$ labeled derivative, said $X^{10}$ labeled derivative, said $X^{11}$ labeled derivative, said $X^{12}$ labeled derivative, said $X^{13}$ labeled derivative, said $X^{14}$ labeled derivative, said $X^{15}$ labeled derivative, said $X^{16}$ labeled derivative, said $X^{17}$ labeled derivative, said $X^{18}$ labeled derivative, and said $X^{19}$ labeled derivative is present and is said donor.

8. The peptide of claim 7, wherein there is no labeled derivative within two amino acids from z.

9. The peptide of claim 7, wherein there is no labeled derivative within five amino acids from z.

10. The peptide of claim 3, wherein $X^{17}$ is said labeled derivative thereof and $X^1$ and $X^{17}$ are an acceptor and a donor fluorescence resonance energy transfer pair.

* * * * *

UNITED STATES PATENT AND TRADEMARK OFFICE
CERTIFICATE OF CORRECTION

PATENT NO. : 6,955,891 B2  Page 1 of 1
APPLICATION NO. : 10/424954
DATED : October 18, 2005
INVENTOR(S) : Cunningham, B. et al.

It is certified that error appears in the above-identified patent and that said Letters Patent is hereby corrected as shown below:

Column 1,
Lines 59-60, "$X^1-X^2-X^3-X^4-X^5-X^6-X^7-X^8-X^9-X^{10}-X^{11}-X^{12}-X^{13}-X^{14}-X^{15}-X^{16}-X^{17}-X^{18}-X^{19}$" should read
-- $X^1-X^2-X^3-X^4-X^5-X^6-X^7-X^8-z-X^9-X^{10}-X^{11}-X^{12}-X^{13}-X^{14}-X^{15}-X^{16}-X^{17}-X^{18}-X^{19}$ --.

Column 3,
Lines 66-67, "$X^1-X^2-X^3-X^4-X^5-X^6-X^7-X^8-X^9-X^{10}-X^{11}-X^{12}-X^{13}-X^{14}-X^{15}-X^{16}-X^{17}-X^{18}-X^{19}$" should read
-- $X^1-X^2-X^3-X^4-X^5-X^6-X^7-X^8-z-X^9-X^{10}-X^{11}-X^{12}-X^{13}-X^{14}-X^{15}-X^{16}-X^{17}-X^{18}-X^{19}$ --.

Column 19,
Lines 49-50, "X 14 is either alanine or said X 14 labeled derivative thereof;" should read
-- $X^{14}$ is either alanine or said $X^{14}$ labeled derivative thereof; --.

Column 20,
Lines 7-8, "$X^1-X^2-X_3-X^4-X^5-X^6-X^7-X^8-X^9-X^{10}-X^{11}-X^{12}-X^{13}-X^{14}-X^{15}-X^{16}-X^{17}-X^{18}-X^{19}$" should read
-- $X^1-X^2-X^3-X^4-X^5-X^6-X^7-X^8-X^9-X^{10}-X^{11}-X^{12}-X^{13}-X^{14}-X^{15}-X^{16}-X^{17}-X^{18}-X^{19}$ --.

Column 20,
Line 10, "wherein $X^1$ is labeled derivative of norleucine;" should read
-- wherein $X^1$ is said $X^1$ labeled derivative of norleucine; --.

Signed and Sealed this

Twenty-seventh Day of June, 2006

JON W. DUDAS
*Director of the United States Patent and Trademark Office*

SEQUENCE LISTING

<160> NUMBER OF SEQ ID NOS: 10

<210> SEQ ID NO 1
<211> LENGTH: 19
<212> TYPE: PRT
<213> ORGANISM: Artificial Sequence
<220> FEATURE:
<223> OTHER INFORMATION: lethal factor substrate
<220> FEATURE:
<221> NAME/KEY: MOD_RES
<222> LOCATION: (1)...(1)
<223> OTHER INFORMATION: Xaa = norleucine labeled with 5,6-carboxyfluoresceinyl

```
<220> FEATURE:
<221> NAME/KEY: AMIDATION
<222> LOCATION: (19)...(19)

<400> SEQUENCE: 1

Xaa Pro Lys Lys Lys Pro Thr Pro Ile Gln Leu Asn Pro Ala Pro Asp
 1               5                  10                  15

Lys Gly Gly

<210> SEQ ID NO 2
<211> LENGTH: 19
<212> TYPE: PRT
<213> ORGANISM: Artificial Sequence
<220> FEATURE:
<223> OTHER INFORMATION: lethal factor substrate
<220> FEATURE:
<221> NAME/KEY: MOD_RES
<222> LOCATION: (1)...(1)
<223> OTHER INFORMATION: Xaa = norleucine labeled with
     5,6-carboxyfluoresceinyl
<220> FEATURE:
<221> NAME/KEY: AMIDATION
<222> LOCATION: (19)...(19)

<400> SEQUENCE: 2

Xaa Lys Lys Lys Lys Val Leu Pro Ile Gln Leu Asn Ala Ala Thr Asp
 1               5                  10                  15

Lys Gly Gly

<210> SEQ ID NO 3
<211> LENGTH: 19
<212> TYPE: PRT
<213> ORGANISM: Artificial Sequence
<220> FEATURE:
<223> OTHER INFORMATION: lethal factor substrate
<220> FEATURE:
<221> NAME/KEY: MOD_RES
<222> LOCATION: (1)...(1)
<223> OTHER INFORMATION: Xaa = norleucine labeled with
     7-hydroxy-4-methyl-3-acetylcoumarinyl
<220> FEATURE:
<221> NAME/KEY: MOD_RES
<222> LOCATION: (17)...(17)
<223> OTHER INFORMATION: Xaa = lysine labeled with
     N-([55 4-[8 (7-nitro-2,1,3-benzoxadiazol-4-yl)amino[9 phe
     nyl[56 acetyl
<220> FEATURE:
<221> NAME/KEY: AMIDATION
<222> LOCATION: (19)...(19)

<400> SEQUENCE: 3

Xaa Lys Lys Lys Lys Val Leu Pro Ile Gln Leu Asn Ala Ala Thr Asp
 1               5                  10                  15

Xaa Gly Gly

<210> SEQ ID NO 4
<211> LENGTH: 19
<212> TYPE: PRT
<213> ORGANISM: Artificial Sequence
<220> FEATURE:
<223> OTHER INFORMATION: lethal factor substrate
<220> FEATURE:
<221> NAME/KEY: MOD_RES
<222> LOCATION: (1)...(1)
<223> OTHER INFORMATION: Xaa = norleucine labeled with
     N-([55 4-[8 (7-nitro-2,1,3-benzoxadiazol-4-yl)amino]9 phe
     nyl[56 acetyl
<220> FEATURE:
<221> NAME/KEY: MOD_RES
<222> LOCATION: (17)...(17)
```

```
<223> OTHER INFORMATION: Xaa = lysine labeled with
      7-hydroxy-4-methyl-3-acetylcoumarinyl
<220> FEATURE:
<221> NAME/KEY: AMIDATION
<222> LOCATION: (19)...(19)

<400> SEQUENCE: 4

Xaa Lys Lys Lys Lys Val Leu Pro Ile Gln Leu Asn Ala Ala Thr Asp
1               5                   10                  15

Xaa Gly Gly

<210> SEQ ID NO 5
<211> LENGTH: 19
<212> TYPE: PRT
<213> ORGANISM: Artificial Sequence
<220> FEATURE:
<223> OTHER INFORMATION: lethal factor substrate
<220> FEATURE:
<221> NAME/KEY: MOD_RES
<222> LOCATION: (1)...(1)
<223> OTHER INFORMATION: Xaa = norleucine labeled with
      7-hydroxy-4-methyl-3-acetylcoumarinyl
<220> FEATURE:
<221> NAME/KEY: MOD_RES
<222> LOCATION: (17)...(17)
<223> OTHER INFORMATION: Xaa = lysine labeled with
      4-dimethylaminoazobenzene-4'-carboxyl
<220> FEATURE:
<221> NAME/KEY: AMIDATION
<222> LOCATION: (19)...(19)

<400> SEQUENCE: 5

Xaa Lys Lys Lys Lys Val Leu Pro Ile Gln Leu Asn Ala Ala Thr Asp
1               5                   10                  15

Xaa Gly Gly

<210> SEQ ID NO 6
<211> LENGTH: 19
<212> TYPE: PRT
<213> ORGANISM: Artificial Sequence
<220> FEATURE:
<223> OTHER INFORMATION: lethal factor substrate
<220> FEATURE:
<221> NAME/KEY: MOD_RES
<222> LOCATION: (1)...(1)
<223> OTHER INFORMATION: Xaa = norleucine labeled with
      4-dimethylaminoazobenzene-4[40 -carboxyl
<220> FEATURE:
<221> NAME/KEY: MOD_RES
<222> LOCATION: (17)...(17)
<223> OTHER INFORMATION: Xaa = lysine labeled with
      7-hydroxy-4-methyl-3-acetylcoumarinyl
<220> FEATURE:
<221> NAME/KEY: AMIDATION
<222> LOCATION: (19)...(19)

<400> SEQUENCE: 6

Xaa Lys Lys Lys Lys Val Leu Pro Ile Gln Leu Asn Ala Ala Thr Asp
1               5                   10                  15

Xaa Gly Gly

<210> SEQ ID NO 7
<211> LENGTH: 16
<212> TYPE: PRT
<213> ORGANISM: Artificial Sequence
<220> FEATURE:
<223> OTHER INFORMATION: lethal factor substrate
<220> FEATURE:
<221> NAME/KEY: MOD_RES
<222> LOCATION: (1)...(1)
```

```
<223> OTHER INFORMATION: Xaa = methionine labeled with
      5,6-carboxyfluoresceinyl
<220> FEATURE:
<221> NAME/KEY: AMIDATION
<222> LOCATION: (16)...(16)

<400> SEQUENCE: 7

Xaa Pro Lys Lys Lys Pro Thr Pro Ile Gln Leu Asn Pro Ala Pro Asp
1               5                   10                  15

<210> SEQ ID NO 8
<211> LENGTH: 8
<212> TYPE: PRT
<213> ORGANISM: Artificial Sequence
<220> FEATURE:
<223> OTHER INFORMATION: lethal factor substrate
<220> FEATURE:
<221> NAME/KEY: MOD_RES
<222> LOCATION: (1)...(1)
<223> OTHER INFORMATION: Xaa = methionine labeled with
      5,6-carboxyfluoresceinyl

<400> SEQUENCE: 8

Xaa Pro Lys Lys Lys Pro Thr Pro
1               5

<210> SEQ ID NO 9
<211> LENGTH: 19
<212> TYPE: PRT
<213> ORGANISM: Artificial Sequence
<220> FEATURE:
<223> OTHER INFORMATION: lethal factor substrate
<220> FEATURE:
<221> NAME/KEY: MOD_RES
<222> LOCATION: (1)...(1)
<223> OTHER INFORMATION: Xaa = norleucine labeled with
      5,6-carboxyfluoresceinyl
<220> FEATURE:
<221> NAME/KEY: MOD_RES
<222> LOCATION: (17)...(17)
<223> OTHER INFORMATION: Xaa = lysine labeled with QSY-9
<220> FEATURE:
<221> NAME/KEY: AMIDATION
<222> LOCATION: (19)...(19)

<400> SEQUENCE: 9

Xaa Lys Lys Lys Lys Val Leu Pro Ile Gln Leu Asn Ala Ala Thr Asp
1               5                   10                  15

Xaa Gly Gly

<210> SEQ ID NO 10
<211> LENGTH: 19
<212> TYPE: PRT
<213> ORGANISM: Artificial Sequence
<220> FEATURE:
<223> OTHER INFORMATION: lethal factor substrate
<220> FEATURE:
<221> NAME/KEY: MOD_RES
<222> LOCATION: (1)...(1)
<223> OTHER INFORMATION: Xaa = norleucine labeled with QSY-9
<220> FEATURE:
<221> NAME/KEY: MOD_RES
<222> LOCATION: (17)...(17)
<223> OTHER INFORMATION: Xaa = lysine labeled with 5,6-
      carboxyfluoresceinyl
<220> FEATURE:
<221> NAME/KEY: AMIDATION
<222> LOCATION: (19)...(19)

<400> SEQUENCE: 10
```

-continued

```
Xaa Lys Lys Lys Lys Val Leu Pro Ile Gln Leu Asn Ala Ala Thr Asp
1               5                   10                  15
Xaa Gly Gly
```